United States Patent [19]

Jacobsen et al.

[11] Patent Number: 5,037,380
[45] Date of Patent: Aug. 6, 1991

[54] IONTOPHORETIC ELECTRODE WITH SOLUTION CONTAINMENT SYSTEM

[75] Inventors: Stephen C. Jacobsen; Tomasz J. Petelenz; Jon Beck; Robert L. Stephen, all of Salt Lake City, Utah

[73] Assignee: Iomed, Inc., Salt Lake City, Utah

[21] Appl. No.: 572,477

[22] Filed: Aug. 23, 1990

Related U.S. Application Data

[62] Division of Ser. No. 349,489, May 9, 1989, Pat. No. 4,968,297.

[51] Int. Cl.⁵ ............................................. A61N 1/30
[52] U.S. Cl. ..................................... 604/20; 604/307; 128/803
[58] Field of Search ................. 604/20, 304, 306, 307, 604/308; 128/803

[56] References Cited

U.S. PATENT DOCUMENTS

| 2,126,070 | 8/1938 | Wappler | 604/20 |
| 4,141,359 | 2/1979 | Jacobsen et al. | 604/20 |
| 4,166,457 | 9/1979 | Jacobsen et al. | 604/20 X |
| 4,419,092 | 12/1983 | Jacobsen et al. | 604/20 |
| 4,911,688 | 3/1990 | Jones | 604/20 |

*Primary Examiner*—Lee S. Cohen
*Attorney, Agent, or Firm*—Thorpe, North & Western

[57] ABSTRACT

An iontophoretic bioelectrode includes a pouch for holding a solution, a receptacle element disposed in a wall of the pouch to allow communication therethrough from the exterior to the interior of the pouch, a pair of elongate, generally parallel prongs joined at one end and dimensioned to allow insertion thereof through the receptacle element into the interior of the container, and a solution absorbing material disposed between the prongs to absorb solution with which it makes contact.

3 Claims, 1 Drawing Sheet

IONTOPHORETIC ELECTRODE WITH SOLUTION CONTAINMENT SYSTEM

This is a division of application Ser. No. 349,489, filed May 9, 1989, now U.S. Pat. No. 4,968,297.

BACKGROUND OF THE INVENTION

This invention relates to a system for containing and thereby preventing the leaking of solution from an iontophoretic bioelectrode or the like.

Iontophoretic bioelectrodes, used in place of hypodermic needles to inject drugs and medication into a person's skin or tissue, typically include a pouch or similar enclosure formed with a wettable barrier or a microporous membrane on one side thereof. See, for example, U.S. Pat. Nos. 4,250,878, 4,419,092 and 4,477,971. A medication solution containing ions to be delivered into the person's skin or tissue is injected into the pouch. When the wettable barrier or membrane is placed against a person's skin and an electric current is supplied to the solution, the ions are caused to migrate from the solution, through the wettable barrier or membrane, and into the skin.

The membrane is adapted to prevent the flow therethrough of solution while allowing movement therethrough of ions. The membrane thus prevents leakage of solution during and after use, and is thus substantially "mess" free. The wettable barrier, on the other hand, although less costly than the membrane, does not prevent leakage of solution and so must be covered until time of use. After use and removal of the pouch from the skin, unused solution would remain on the skin, drip or run on the skin, possibly stain a patient's clothing, and generally cause a mess. It would thus be desirable to somehow contain this solution and prevent it from escaping from the pouch, without requiring use of expensive membranes.

SUMMARY OF THE INVENTION

It is an object of the invention to provide an inexpensive iontophoretic bioelectrode with a solution containment feature.

It is also an object of the invention to provide a simple, easy to manufacture, and easy to use system for containing solution left over after use of an iontophoretic bioelectrode or similar solution administering device.

It is another object of the invention to provide such a system capable of containing the solution within the administering device.

The above and other objects of the invention are realized in a specific illustrative embodiment of a solution containment system for use in connection with an ion-delivery pouch into which solution is to be introduced, at least some of which is to be contained or prevented from leaving the pouch. The system includes a receptacle element disposed in a wall of the pouch to allow communication therethrough from the exterior to the interior of the pouch, and a solution absorbing device for insertion through the receptacle element into the interior of the pouch, and for absorbing solution with which it makes contact. In accordance with one aspect of the invention, the solution absorbing device includes a pair of elongate, generally parallel prongs joined at one end and dimensioned to allow insertion thereof through the receptacle element into the interior of the container. The solution absorbing device also includes a solution absorbing material disposed between the parallel prongs.

BRIEF DESCRIPTION OF THE DRAWINGS

The above and other objects, features, advantages and alternative aspects of the invention will become apparent from a consideration of the following detailed description presented in connection with the accompanying drawings in which.

DETAILED DESCRIPTION

Figure 1:
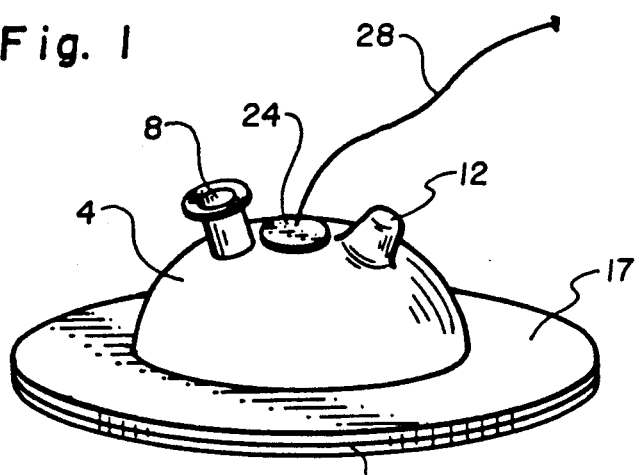
FIG. 1 shows a perspective view of an iontophoretic bioelectrode with a solution containment system made in accordance with the principles of the present invention.
Figure 2:
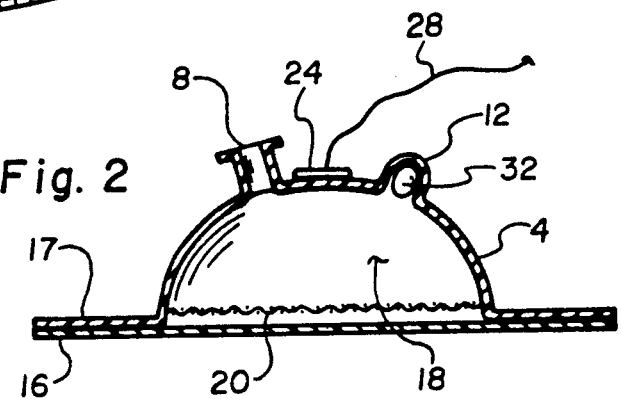
FIG. 2 shows a side, elevational, cross-sectional view of the bioelectrode and system of FIG. 1.

Referring to FIGS. 1 and 2, there is shown a bioelectrode composed of a generally dome-shaped upper wall 4 which may be made of plastic, polyvinyl chloride, polyurethane, or other material suitable for holding a solution. Mounted on the upper wall 4 is a receptacle structure (add-site) 8 through which ion-containing solution is introduced into the bioelectrode. Such structure is well-known and is described, for example, in U.S. Pat. Nos. 4,250,878 and 4,419,092. Also formed in the upper wall 4 is a nipple or blister 12 which will be discussed momentarily.

The bioelectrode of FIGS. 1 and 2 also includes a protective cover 16 secured by a releasable adhesive to the bottom surface of the perimeter edges of the upper wall 4. The bottom surface of the perimeter edges 17 of the upper wall 16 also include an adhesive so that when the protective cover 16 is removed, the upper wall may be attached to the skin of a person to be treated. The protective cover 16 could be simple plastic, treated paper, or other suitable covering material. A piece of mesh material 20 covers the opening of the dome-shaped portion of the upper wall 4 (for reasons to be discussed later) to define an interior cavity 18 in the bioelectrode. The mesh material could be simple gauze, porous plastic, or some other material which would allow the passage therethrough of solution.

Mounted on the exterior of the upper wall 4 is an electrode plate 24. The electrode plate 24 extends over a reasonable portion of the upper wall 4 and is attached to maintain electrical contact with the wall. An adhesive or strap may be used to attach the electrode. Electrically coupled to the electrode plate 24 is a conductor 28 leading to a potential source (not shown), all in a well-known manner. Of course, there are a variety of other arrangements for providing and attaching the electrode plate to the bioelectrode.

Disposed in the nipple 12 is a capsule 32 containing liquid absorbent in the form of dry gel, powder, pellet, laminate or the like, capable of absorbing a substantial amount of liquid with which it comes in contact. Examples of absorbent materials which could be used include super-absorbent polyacrylates and polyacrylamides. The capsule 32 advantageously is held in place in the nipple 12 simply by close forming the nipple about the capsule during manufacture or by forming the nipple to be slightly smaller in diameter than the capsule, but with the nipple being sufficiently elastic to yield and allow insertion of the capsule after manufacture. The capsule 32 might illustratively be constructed of a thin plastic material such as polypropylene or polycarbonate. The capsule 32 could be formed either as a complete enclosure, with no openings, but be made of a burstable material, so that when disposed in the nipple 12 and when squeezed manually by a user, the wall of the capsule would burst to release the contents thereof into the cavity 18 of the bioelectrode.

Alternatively, the capsule 32 could be constructed with an opening on one side and then the capsule, with liquid absorbent material contained therein, placed in the nipple 12 with the capsule opening facing away from the cavity 18 of the bioelectrode. The entire capsule 32 could then be squeezed from the nipple 12 into the cavity 18 to perform the liquid or solution absorbing function.

In use, the protective cover 20 would be removed from the bottom of the bioelectrode and then the upper wall 4, namely the perimeter edges 17 of the upper wall, placed against the skin of a person to be treated. The perimeter edges 17 would be pressed down against the skin to form as tight a seal as possible. With the bioelectrode in place, the medication solution would be supplied to the cavity 18 of the bioelectrode via the receptacle or add-site 8, for example, using a hypodermic needle or other solution injection device. After supplying the medication solution to the bioelectrode, an electric current would be supplied via conductor 28 to the electrode 24 to produce an electric field for causing ions in the solution to migrate into the person's skin as desired.

After the completion of the ionopheretic delivery of ions into the skin of the person, the nipple 12 is squeezed to either burst the capsule 32 releasing the absorbent material into the cavity 18, or to force the capsule 32 from the nipple into the cavity 18, which, in either case, exposes the absorbent material to any solution remaining in the cavity 18. The absorbent material, whether a gel, powder, pellet, laminate, etc., swells as it absorbs the remaining solution and remains as a single mass, held in the cavity 18 by the retaining mesh material 20. The bioelectrode may then be removed from the skin, leaving no messy left-over medication for unauthorized reuse.

Figure 3:
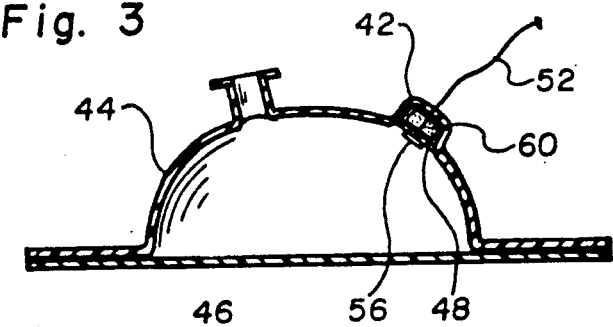
FIG. 3 shows a side, elevational, cross-sectional view of another embodiment of a solution containment system made in accordance with the principles of the present invention.

FIG. 3 shows a side, elevational, cross-sectional view of another embodiment of a solution containment system having the same general structure as that of FIGS. 1 and 2. The difference is that the system of FIG. 3 includes a pocket 42 formed in an upper wall 44 of the bioelectrode. Covering the opening of the pocket 42, to separate the interior of the pocket from the interior 46 of the bioelectrode, is a septum 48 made, for example, of thin polyurethane. The septum 48 could, illustratively, be secured over the pocket opening by a suitable adhesive. A tether or break string 52 extends through an opening in the top of the pocket 42 and through the septum 48 where it is joined to a rigid button 56. Disposed in the pocket 42 above the septum 48 is a highly compressed, but resilient sponge 60, such as a compressed cellulose sponge. The size of the pocket 42 and position of the septum 48 maintain the sponge 60 in the compressed state until the break string 52 is pulled which causes the button 56 to press against and break the septum 48. With the septum 48 broken, the compressed sponge 60 is released to expand out of the pocket and into the cavity 46 where it will absorb solution with which it comes in contact. This, of course, would occur after iontophoretic delivery of medication into a person's skin or tissue.

Figure 4:
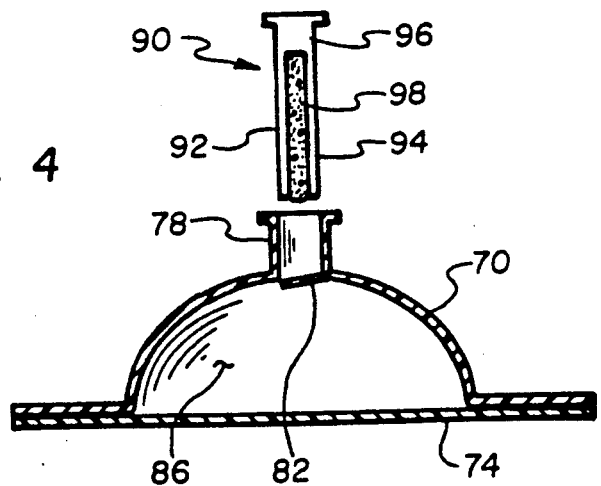
FIG. 4 is a side, elevational, cross-sectional view of still another embodiment of a solution containment system made in accordance with the principles of the invention.

FIG. 4 shows a side, elevational, cross-sectional view of still another embodiment of a solution containment system which includes an upper wall 70 formed with the same shape as the bioelectrodes of FIGS. 1 and 2 and FIG. 3, and a protective cover 74. A larger generally cylindrical receptacle 78 is located generally at the top of the upper wall 70 and includes a resilient flap 82 which is attached at one side to a side of the receptacle to normally cover the entrance of the receptacle to the interior 86 of the bioelectrode. The receptacle 78 may be used both to introduce medication solution into the cavity 86 and to provide for entrance of a solution absorbing element.

The solution absorbing element, in this embodiment, comprises an elongate clothes pin shaped sponge holder 90 having a pair of elongate, generally parallel prongs 92 and 94 joined at one end 96. The sponge holder 90 is dimensioned to allow insertion thereof through the receptacle 78 into the interior 86 of the bioelectrode of FIG. 4. Disposed between the prongs 92 and 94 is an elongate compressed sponge 98, such as a cellulose sponge.

After use of the bioelectrode of FIG. 4, the elongate sponge holder 90 would be inserted through the receptacle 78, pushing aside the flap 82, into the interior 86 of the bioelectrode. The sponge holder 90 would then be moved about in the cavity 86 to contact left-over medication solution to thereby absorb such solution (in the sponge 98), and allow for the clean removal of the bioelectrode from the person's skin.

In the manner described, various embodiments of a solution containment system provide for the prevention of spilling, dripping or running of left-over medication after removal of a bioelectrode from use on a person's skin. In all embodiments, a solution absorbing element or material is ultimately injected into the cavity of the bioelectrode to contact and absorb left-over solution.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:
1. An iontophoretic bioelectrode comprising
   a pouch for holding a solution,
   a receptacle element disposed in a wall of the pouch to allow communication therethrough from the exterior to the interior of the pouch, and
   a solution absorbing means for insertion through the receptacle element into the interior of the pouch, and for absorbing solution with which it makes contact.
2. An electrode as in claim 1 wherein said solution absorbing means comprises a pair of elongate, generally parallel prongs joined at one end and dimensioned to allow insertion thereof through the receptacle element into the interior of the container, and solution absorbing material disposed between the prongs.
3. An electrode as in claim 2 wherein said solution absorbing material is sponge.